US012124538B2

(12) United States Patent
Dickie et al.

(10) Patent No.: US 12,124,538 B2
(45) Date of Patent: Oct. 22, 2024

(54) METHOD AND SYSTEM FOR TRAINING AND DEPLOYING AN ARTIFICIAL INTELLIGENCE MODEL ON PRE-SCAN CONVERTED ULTRASOUND IMAGE DATA

(71) Applicant: Clarius Mobile Health Corp., Vancouver (CA)

(72) Inventors: Kris Dickie, Vancouver (CA); Parisa Asgharzadeh, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 598 days.

(21) Appl. No.: 17/187,851

(22) Filed: Feb. 28, 2021

(65) Prior Publication Data
US 2022/0277175 A1     Sep. 1, 2022

(51) Int. Cl.
| G06F 18/21 | (2023.01) |
| A61B 8/00 | (2006.01) |
| A61B 8/08 | (2006.01) |
| G06T 7/10 | (2017.01) |

(52) U.S. Cl.
CPC ............ *G06F 18/2178* (2023.01); *A61B 8/08* (2013.01); *A61B 8/085* (2013.01); *A61B 8/0875* (2013.01); *A61B 8/461* (2013.01); *A61B 8/5207* (2013.01); *G06T 7/10* (2017.01); *G06T 2207/10132* (2013.01); *G06T 2207/20081* (2013.01); *G06T 2207/30008* (2013.01); *G06T 2207/30096* (2013.01)

(58) Field of Classification Search
CPC ........................ G06T 2207/20081; G06T 7/10
See application file for complete search history.

(56) References Cited

U.S. PATENT DOCUMENTS

| 2019/0159737 A1* | 5/2019 | Buckler ................. G16H 50/50 |
| 2019/0220701 A1* | 7/2019 | Novak ............. G06V 30/19173 |
| 2019/0269384 A1* | 9/2019 | Lundberg ............... A61B 8/585 |
| 2019/0282208 A1* | 9/2019 | Silberman ............. G06T 7/0012 |
| 2020/0043602 A1* | 2/2020 | Kim ......................... G06N 3/02 |
| 2020/0226422 A1* | 7/2020 | Li ............................. G06N 3/04 |

(Continued)

OTHER PUBLICATIONS

J. Wang et al, "Capacitive micromachined ultrasound transducers for intravascular ultrasound imaging", Microsystems and Nanoengineering, vol. 6, No. 73, pp. 1-13, 2020 (Year: 2020).*

*Primary Examiner* — Joel Lamprecht
*Assistant Examiner* — Nyrobi Celestine
(74) *Attorney, Agent, or Firm* — Julian Ho; Susan Ben-Oliel (57) ABSTRACT

Post-scan ultrasound images are masked and labeled with anatomical features identified in the images. Masks corresponding to the features are transformed into the coordinate system of the pre-scan, raw ultrasound data frames corresponding to the images. The masks and their respective raw ultrasound data frames are used to train an artificial intelligence model. The model is then used to predict the presence of anatomical features of the same type in other pre-scan ultrasound data. Once predicted, the raw data is scan converted for display as segmented ultrasound images that identify the predicted anatomical features. Deployment of the model on pre-scan data avoids the need to account for different levels of processing that may be applied to post-scan images, while the labeling for training the model may be done on the post-scan images.

20 Claims, 7 Drawing Sheets

(56) References Cited

U.S. PATENT DOCUMENTS

| | | | |
|---|---|---|---|
| 2020/0294659 A1* | 9/2020 | Gopinath | A61B 34/10 |
| 2020/0315587 A1* | 10/2020 | Toporek | A61B 8/5269 |
| 2020/0401832 A1* | 12/2020 | Peng | G16H 50/20 |
| 2021/0177373 A1* | 6/2021 | Xie | G06N 3/04 |
| 2021/0212665 A1* | 7/2021 | Tsymbalenko | A61B 8/5223 |

* cited by examiner

METHOD AND SYSTEM FOR TRAINING AND DEPLOYING AN ARTIFICIAL INTELLIGENCE MODEL ON PRE-SCAN CONVERTED ULTRASOUND IMAGE DATA

TECHNICAL FIELD

This disclosure relates to ultrasound imaging. In particular, it relates to systems and methods for training and deploying an artificial intelligence (AI) model on pre-scan converted ultrasound image data.

BACKGROUND

Ultrasound is a useful, non-invasive imaging technique capable of producing real time images of internal structures within tissue. Ultrasound imaging has an advantage over X-ray imaging in that ultrasound imaging does not involve ionizing radiation. Some mobile ultrasound scanners, including app-based ultrasound scanners, communicate with an add-on device that can act as both as a display and a control device. Examples of these add-on devices are mobile phones, tablets, laptops, or desktop computers.

Skilled ultrasound operators are required to obtain suitable ultrasound images (i.e. post-scan images), which then must be interpreted to identify specific anatomical features. As it may be difficult to interpret ultrasound images, AI models may be run on the ultrasound images to predict the presence of, and identify, specific anatomical features. The output of the AI model is typically an ultrasound image that is segmented to delineate or otherwise indicate a predicted anatomical feature in the image.

AI models need to take into account, for example, different screen sizes, pixel sizes, zooming, aspect ratios and blackened areas around the ultrasound image. For example, typical ultrasound images have a considerable amount of black space. E.g., in an ultrasound image generated from a curvilinear scanner, the ultrasound image may reflect the curvature of the probe head at the top of the image and/or there may be black areas on the upper left and right corners of an ultrasound image (see e.g., FIG. 8). The sizes of these black spaces also vary based on image depth.

The same may also be true for ultrasound images acquired using a linear scanner: the aspect ratio of an image may differ based on the image depth. A shallow image may generally be displayed as wide and short, whereas a deep image may be displayed as tall and narrow. It is possible that some or all of these differences in high an ultrasound image is displayed may reduce the efficiency of training the AI model and/or may reduce the accuracy of the AI predictions.

For example, the variations in how ultrasound images are displayed, even for the same scanner type, may make the training of the AI model more difficult by increasing the time it takes to converge or by possibly not leading to convergence at all. This may be because, generally, images with the same dimensions are used to train AI models. However, even if images with the same dimensions are used to train the AI model, and such images include those acquired with various image depths, the amount of black space will vary greatly, and this may confuse the training of an AI model.

Further, labeling of ultrasound images for the training of AI models is generally done on post-scan converted images, which have x-y coordinates. It is not known to label raw (i.e. pre-scan converted) ultrasound data frames with anatomical features for the purpose of training AI models. It is also not known to generate raw ultrasound data frames that are segmented or labeled with predictions of anatomical features.

The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

DETAILED DESCRIPTION

A. Glossary

The term "AI model" means a mathematical or statistical model that may be generated through artificial intelligence techniques such as machine learning and/or deep learning. For example, these techniques may involve inputting labeled or classified data into a neural network (e.g., a deep neural network) algorithm for training, so as to generate a model that can make predictions or decisions on new data without being explicitly programmed to do so. Different software tools (e.g., TensorFlow™, PyTorch™, Keras™) may be used to perform machine learning processes.

The term "anatomical feature" means any part of a human body, an animal, or phantom, and may refer to an entire organ, a part of an organ, damage to an organ, abnormality of an organ, illness, an unwanted growth, and the like.

The term "back converting" means to perform a reverse scan conversion, which is to convert an ultrasound image back to its corresponding raw ultrasound data frame, or to a raw ultrasound data frame in a standardized format. The standardized format may be defined, for example, by a fixed number of scan lines and a fixed number of samples in each scan line. Back converting may also apply to markings made on an ultrasound image, which may delineate an anatomical feature, in which case the coordinates of the markings are transformed from the coordinate system of the ultrasound image to the coordinate system of the raw ultrasound data frame. The back converting of markings and their insertion, combination or association with a raw ultrasound data frame may be considered to be an interpolation of the markings into the raw ultrasound data frame.

The term "interpolating" means to back convert markings or their coordinates, which may delineate an anatomical feature on an ultrasound image, from the coordinate system of the ultrasound image to the coordinate system of a raw ultrasound data frame and insert, combine or otherwise associate them with the raw ultrasound data frame.

The term "labeling" refers to an act by a human user to label a piece of training data. For example, a user may mark a feature on an ultrasound image and identify the anatomy to which the feature corresponds. The result is a labeled piece of data, such as a labeled ultrasound image. If this image is then back converted to raw data coordinates, then the resulting raw ultrasound data may be referred to as labeled raw ultrasound data or a labeled raw ultrasound data frame.

The term "raw ultrasound data" or "raw ultrasound data frame" means a frame of lines of ultrasound scan data representing echoes of ultrasound signals acquired by an ultrasound scanner. The data is organized or stored using raw data coordinates, which is a typical form of the data prior to being scan converted.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (x-y) coordinates.

The term "system" as used herein, unless otherwise qualified, refers to a system or part of a system according to the invention disclosed herein, e.g., a device (or network of connected devices) that presents a user (e.g. ultrasound labeler) with ultrasound images, receives input from the user that marks and identifies anatomical features in the ultrasound images, back converts the resulting labeled ultrasound images to labeled raw ultrasound data frames, uses the labeled raw ultrasound data frames to train an AI model, uses the AI model to predict the presence of anatomical features in other raw ultrasound data frames, and scan converts these now-labeled raw ultrasound data frames to segmented ultrasound images that identify the predicted anatomical feature.

The term "ultrasound image frame" (or "image frame" or "ultrasound frame") refers to a frame of post-scan conversion data that is suitable for rendering an ultrasound image (or, for brevity, "image") on a screen or other display device.

B. Exemplary Embodiments

At a high level, the embodiments herein generally allow for the AI prediction of anatomical features in pre-scan converted ultrasound image data. The data is then scan converted to result in post-scan converted ultrasound images that are segmented with the predicted anatomical features. Training of the AI model may be performed using labeled raw ultrasound data frames that have been back converted from labeled post-scan converted ultrasound images.

Figure 1:
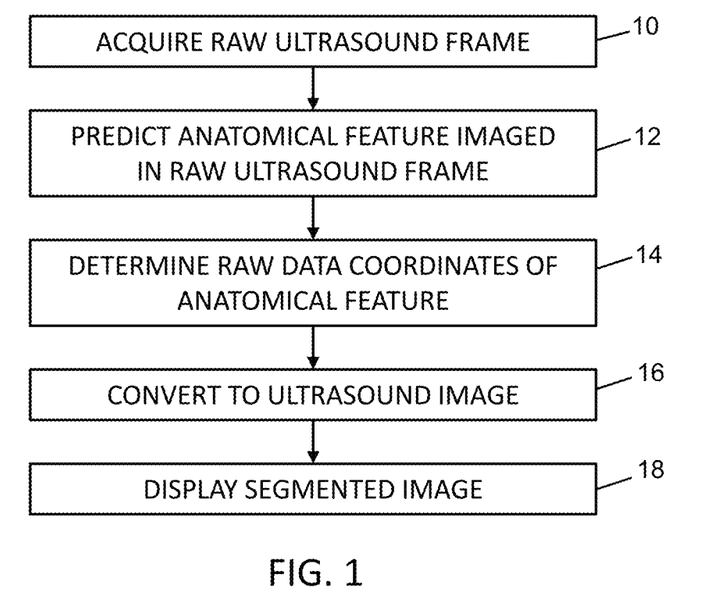
FIG. 1 is a flowchart of the main steps of a method for displaying a segmented ultrasound image with a predicted anatomical feature, according to an embodiment of the present invention.

Referring to FIG. 1, a flowchart is shown of the main steps of a method for displaying a segmented ultrasound image with an anatomical feature that has been predicted in the corresponding raw ultrasound data frame. In step 10, an ultrasound scanner (hereinafter "scanner", "probe", or "transducer" for brevity) is used to acquire a raw ultrasound frame.

In step 12, the raw ultrasound data frame is processed against an AI model, in order to predict the presence of an anatomical feature that is imaged in the raw ultrasound data frame. The anatomical feature may be, for example, an organ, a portion of an organ, a boundary of an organ, a bodily fluid, a tumor, a cyst, a fracture, a break, or the like. As it is the raw ultrasound data frame that is being processed by the AI model, it is not yet scan converted. As a result, the anatomical feature that is imaged would likely be distorted and therefore less recognizable to a human than the same anatomical feature in a post-scan converted image. The AI model may run, for example, on an ASIC (application specific integrated circuit) or an optimized FPGA (field programmable gate array) onboard in the scanner. In other embodiments, the AI model may run on the add-on device (e.g., a mobile display device such as a tablet computer, which may generally be referred to as a display device or smart device herein) to which the acquired raw ultrasound data is sent.

In step 14, the process may then involve determining the raw data coordinates of the predicted anatomical feature in the raw ultrasound data frame. This may be achieved by the AI model identifying the extent of the image of the anatomical feature in the raw ultrasound data frame. The raw data coordinates may be represented by a single point that defines a circle, and/or coordinates that define another geometric shape of predetermined size. Additionally or alternatively, the raw data coordinates may be defined by the corners of a rectangle or other geometric shape enclosing the predicted anatomical feature. Additionally or alternatively, the raw data coordinates may be defined by a series of points that if joined would enclose the predicted anatomical feature, or even a line that encloses the feature. In further embodiments, other ways of delineating or identifying the location of the predicted anatomical feature in the raw ultrasound date frame may be employed.

In step 16, the raw ultrasound data frame with its predicted anatomical feature may then be scan converted to an ultrasound image. This scan conversion may be in one or two steps, for example. The raw ultrasound data frame may be segmented by the coordinates that identify the location of the predicted anatomical feature, for example, so that the raw ultrasound data frame is modified at such coordinates. In this case, the modified raw ultrasound data frame with its predicted anatomical feature may be scan converted to a segmented ultrasound image in one step by scan converting the modified raw ultrasound data frame. In another example, if the raw data coordinates that identify the location of the anatomical feature are kept separate from the raw ultrasound data frame, then the raw ultrasound data frame may be scan converted to an ultrasound image frame in one step and the raw data coordinates resulting from application of the AI model may be transformed to the ultrasound image coordinate system in another step. Converting the raw data coordinates may involve, for example, transforming them from R-theta coordinates of the raw ultrasound data frame to x-y coordinates of the ultrasound image frame.

After the scan conversion, the ultrasound image segmented with a representation of the x-y coordinates of the predicted anatomical feature may, in step 18, be displayed on a screen of a display device. As well, the name of the particular anatomical feature that is predicted may also be displayed on the screen.

One potential benefit of the AI model running on the raw data rather than the post-scan converted ultrasound image may be that issues related to the AI model's ability to adjust for input scaling, screen size, pixel size, aspect ratio, resolution, aspect ratio, and/or dead space (e.g., blackened area) can be avoided. In turn, this may lead to a more robust system and more accurate predictions compared to a similar AI model running on post-scan conversion input data.

Another potential benefit may be that an AI model that runs on raw ultrasound frames can be executed on the ultrasound scanner since scan conversion for screen dimensions, etc. does not have to be performed to apply the AI model. Such a configuration where the AI model is executed on the scanner may reduce the computing workload on the smart device that displays the segmented ultrasound images, since the smart device may no longer need to execute an AI model. In turn, this may reduce the hardware requirements of the smart device (e.g., and allow the AI model to be executed on more models of smart devices) and/or improve responsiveness of the ultrasound application displaying segmented ultrasound images on the smart device.

Figure 2:
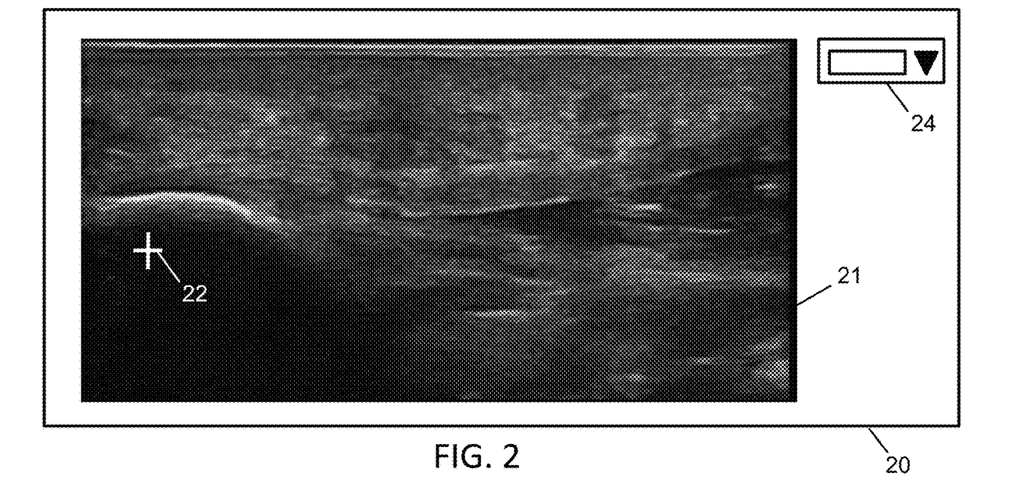
FIG. 2 is a schematic diagram of an example user interface for training an AI model according to an embodiment of the present invention.

Referring to FIG. 2, an example user interface 20 is shown for labeling an ultrasound image 21, which is a post-scan converted image. The user interface 20 may be displayed on a computer, such as a laptop computer, a desktop computer or a tablet. The user interface 20 includes a cursor 22, which the user (e.g., ultrasound labeler, or labeler) may move around over the ultrasound image 21 and, at various points on the image, use it to mark the image. For example, the user may use the cursor 22 to mark individual points around a particular anatomical feature present in the ultrasound image 21, and/or to draw an enclosing line around the particular anatomical feature. Also present in the user interface 20 is a pull-down menu 24, which may list various anatomical features that the user may identify in the ultrasound image 21. In use, the user may mark the anatomical feature with the cursor 22 and label the marked anatomical feature with a corresponding choice from the pull-down menu 24, to result in a labeled training ultrasound image.

Figure 3:
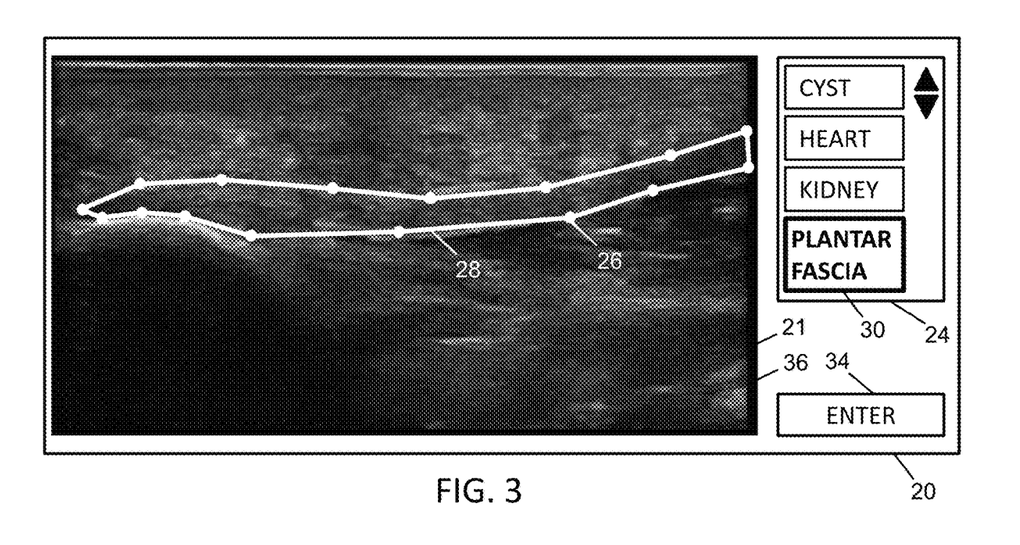
FIG. 3 is a schematic diagram of the example user interface for training an AI model of FIG. 2, showing the labeling of an ultrasound image, according to an embodiment of the present invention.

FIG. 3 shows the user interface 20 after the anatomical feature has been identified and marked. Displayed over the ultrasound image 21 and around the anatomical feature are points 26 that have been created by the user clicking when the cursor 22 was located at those points 26. The points 26 are connected by lines 28 that are generated and displayed by the user interface 20. The lines 28 trace around the anatomical feature, which has been labeled by the user by selecting a named anatomical feature given by an option 30 in the pull-down menu 24, shown here expanded. Non-limiting examples of named anatomical features include "cyst", "heart", "kidney" and "plantar fascia" as shown in the pull-down menu 24. In this example, the anatomical feature identified by the user is a plantar fascia, which is shown by emboldening the selected menu option 30. After the anatomical feature has been marked and labeled, an 'Enter' button 34 is displayed on the user interface 20. The 'Enter' button 34 may be clicked, or otherwise activated, to submit the labeled training ultrasound image 36, with label 30, to the system for back conversion to the format of a raw ultrasound data frame for training the AI model. Back conversion may involve, for example, the lines 28, which may be considered to be a mask, being interpolated back into the raw ultrasound data frame from which the ultrasound image 21 was scan converted. Back conversion may alternately involve back converting both the ultrasound image and the mask to a pre-scan ultrasound data frame format, which may be necessary if the ultrasound image 21 has been obtained from a third party and the underlying raw ultrasound data frame corresponding to the ultrasound image 21 is not available.

In some embodiments, the user interface 20 may use other techniques for marking the anatomical feature. For example circles, ovals, squares, rectangles, and other shapes of mask may be used, or shading or highlighting may be used. The main requirement is that the technique identify the area in the ultrasound image 21 that represents the anatomical feature of interest. The identified area may be expressed, for example, as a range of individual pixels, a regular polygon defined by the pixels at its vertices, an irregular polygon defined by the pixels at its vertices, an enclosed curve that is spline fitted to pixels marked by a user, and/or a freeform shape defined by a combination of fitted curves and straight lines to pixels identified by the user. In some cases, one, some or all of the pixels may be calculated by the system based on smoothing the inputs from the user.

It is not necessary for the user to exactly outline the anatomical feature, as the AI model may compensate for any dither in the marking that the user makes. In some embodiments, the user has the option of editing the individual points 26 or the shape marked on the ultrasound image 21. It is also possible for the user to mark and identify multiple anatomical features in the same ultrasound image 21. Where multiple anatomical features are identified, they may be the same type of anatomical feature, different types of anatomical feature, and/or overlapping anatomical features. Each different type of marking may be used in a separate channel to provide training data to the AI model.

Figure 4:
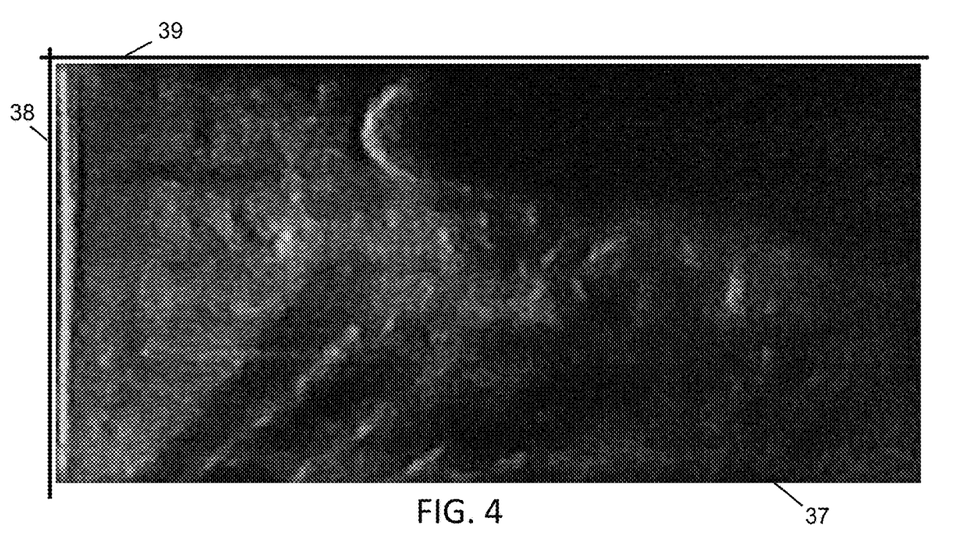
FIG. 4 is a raw ultrasound data frame acquired from scanning the plantar fascia of a foot.

Referring to FIG. 4 we can see a raw ultrasound data frame 37 acquired in a similar scenario to which the ultrasound image 21 shown in FIGS. 2 and 3 was acquired. The difference is that the raw ultrasound data frame 37 is not scan converted, whereas the ultrasound image 21 is scan converted. The raw ultrasound data frame 37 is unsuitable for human display because the details in it are significantly distorted compared to what a human is accustomed to viewing in ultrasound images such as ultrasound image 21. FIG. 4 represents pre-scan ultrasound data acquired using an ultrasound scanner with a linear footprint, so the resulting ultrasound image 21 (e.g., as shown in FIGS. 2 and 3) would generally have a rectangular shape. In FIG. 4, the scanlines are shown as distributed along the y-axis 38 and the samples for a given scanline extend in a direction parallel to the x-axis 39. In contrast, the post-scan ultrasound image 21 shown in FIGS. 2 and 3 is composed of scanlines distributed along the x-axis with the samples in a given scanline parallel to the y-axis to account for the linear footprint of the ultrasound scanner.

Figure 5:
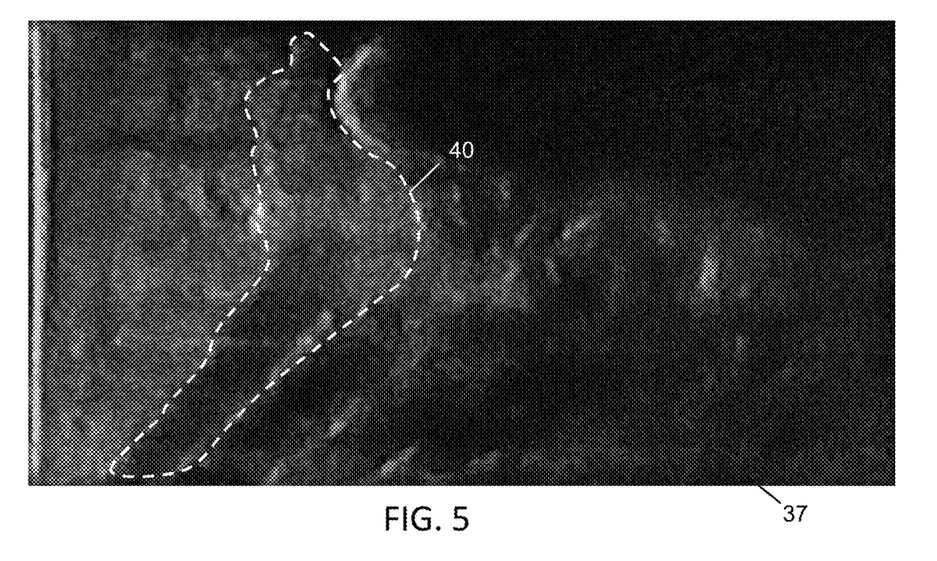
FIG. 5 is the raw ultrasound data frame of FIG. 4 marked with a region of the imaged plantar fascia as predicted by the AI model, according to an embodiment of the present invention.

Referring to FIG. 5, shown there is the raw ultrasound data frame 37 of FIG. 4 with a portion 40 of the data "segmented" after application of an AI model, according to an embodiment of the invention. The raw ultrasound data may not actually exist in this form; it is shown like this in FIG. 5 for illustration purposes only, to show a step of the process in the AI prediction. In use, the AI model may, for example, identify portion 40 of the data as a prediction for the presence of a plantar fascia in the body region that is scanned by the scanner. This prediction may be, for example, based on training inputs such as that shown in FIG. 3 having been provided to the AI model. After the portion 40 of the data has been identified, it is possible to scan convert the raw ultrasound data frame 37 to an ultrasound image suitable for human viewing, and as well transform the coordinates of portion 40 of the data from the coordinate system of the raw ultrasound data frame 37 to the coordinate system of the displayed ultrasound image.

Figure 6:
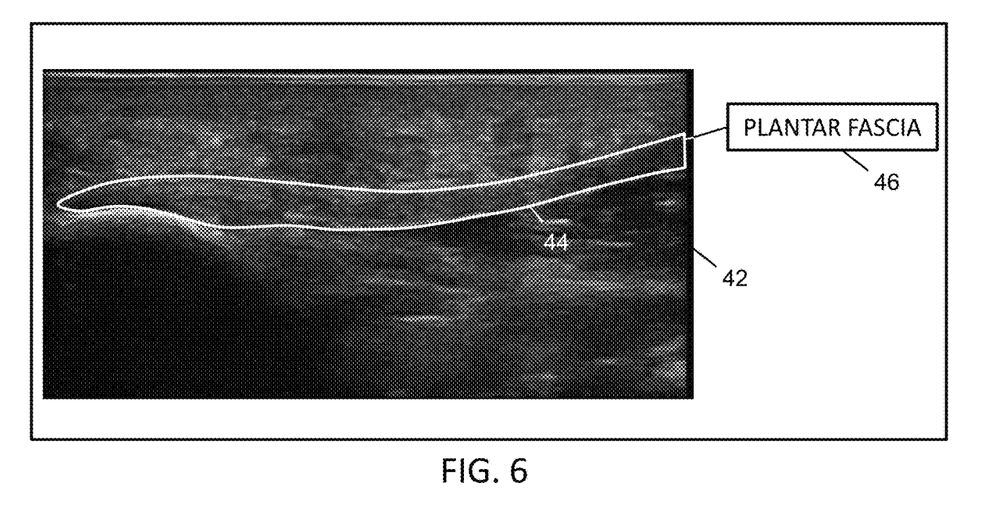
FIG. 6 is a schematic diagram of a user interface displaying a segmented ultrasound image of a plantar fascia after being scan converted from the raw ultrasound image with the imaged plantar fascia identified in FIG. 5, according to an embodiment of the present invention.

FIG. 6 shows a user interface displaying a segmented ultrasound image 42, which is segmented with area 44. The segmented ultrasound image 42 is the result of a scan conversion of the raw ultrasound data frame 37 of FIG. 5. The segmented area 44 corresponds to the portion 40 of the raw ultrasound data frame 37 that is identified by the AI model as its prediction of the presence of a plantar fascia in the raw ultrasound data frame 37. The segmented area 44 is named by tag 46, which identifies the segmented area as a plantar fascia according to the prediction of the AI model.

Referring still to FIG. 6, the perimeter lines defining the segmented area 44 may be superimposed on the ultrasound image 42. In other embodiments, these perimeter lines defining the segmented area 44 may be an integral part of the ultrasound image 42, if corresponding perimeter lines around portion 40 of the raw ultrasound data frame 37 are embedded in the raw ultrasound data frame 37 by the AI model. In other embodiments, the perimeter lines around the segmented area 44 may be toggled on and off in order to allow the viewer of the segmented ultrasound image 42 to see the image in its non-segmented form.

It has been found that the segmentation of raw ultrasound data frames may be more accurate compared to other segmentation processes that employ an AI model that processes post-scan ultrasound images. When segmenting raw ultrasound data frames, there is no dead space to deal with, which would be present around post-scan ultrasound images, and which would vary depending on the geometry and depth of the scan.

Also, segmenting raw ultrasound data frames may be less susceptible to depth variations than segmenting post-scan ultrasound images. For example, if a feature to be segmented is at a 2 cm depth, the appearance of that feature on an image that is acquired at 5 cm may appear different from the appearance of the same feature on an image acquired at 10 cm (e.g., because the feature may form a larger portion of the image acquired in at 5 cm than the image acquired at 10 cm). However, if the AI model is trained on raw ultrasound data frames, the AI model may be able to more easily learn that the feature is present at a certain depth based on scanline and sample data. In turn, this may allow the data in the raw ultrasound data frames to be more easily truncated so as to allow for better performance in both training and running the AI model.

While the present embodiments segment the raw ultrasound data, the labeling for the AI model may still be done on post-scan ultrasound images as noted above with respect to FIGS. 2 and 3. Based on this labeling, masks can be used to interpolate the labeled areas back to pre-scan, raw ultrasound data frames or formats. These now labeled raw ultrasound data frames may have a standardized format, such as a standard number of scanlines and a standard number of samples, and they can be used for training the AI model. If the training data has a standardized format, the AI model will be likely to converge more accurately and more quickly than if a range of different formats were used.

In some embodiments, if a compound ultrasound image is labeled then the AI model may be trained with just the center frame of the compound ultrasound image, after it has been back-converted to the format of a raw ultrasound data frame. This is because the AI model only needs to analyze the central data frame rather than those acquired at an angle. It may also allow the AI model to converge more accurately as it will not need to consider irrelevant data.

The example embodiments discussed above with respect to FIGS. 2-6 have been for raw ultrasound data frames and ultrasound images acquired using an ultrasound scanner with a linear footprint. However, the present embodiments may be employed with ultrasound scanners having any footprint or ultrasound firing sequence, including curvilinear or convex scanners, microconvex scanners, endocavity scanners, and/or phased array scanners.

Figure 7:
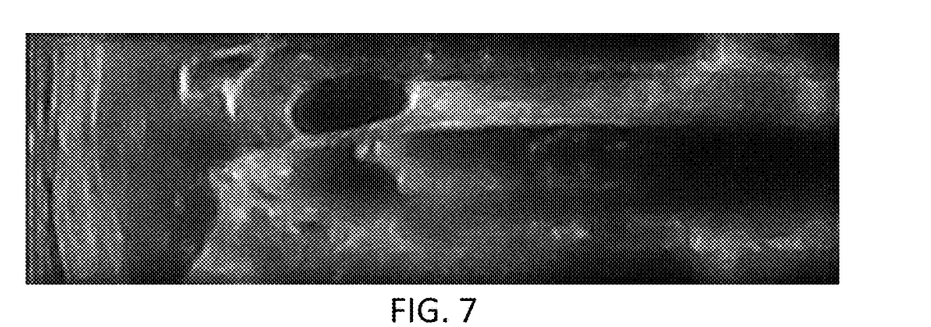
FIG. 7 is a raw ultrasound data frame acquired using an ultrasound scanner with a curved footprint.
Figure 8:
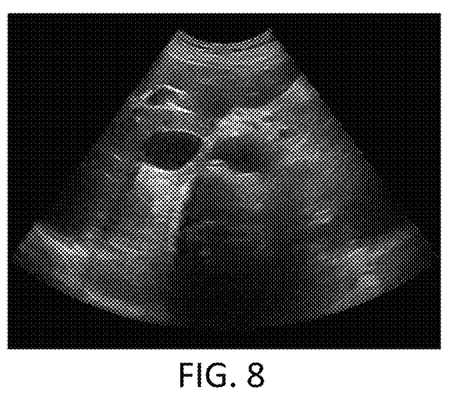
FIG. 8 is the post-scan converted ultrasound image corresponding to the raw ultrasound data frame of FIG. 7.

Referring to FIG. 7, shown there is a raw ultrasound data frame that has been acquired by an ultrasound scanner with a curved footprint, which has been used to scan abdominal tissue. FIG. 8 is the post-scan converted ultrasound image corresponding to the raw ultrasound data frame of FIG. 7. In FIG. 7, the scanlines are shown as distributed along the y-axis and the samples for a given scanline extend parallel to the x-axis. However, similar to FIG. 4 discussed above, FIG. 7 is not suitable for human display because the details in it are significantly distorted compared to what would be representative of the tissue imaged and what a human is accustomed to viewing in ultrasound images acquired using a curvilinear scanner. Particularly, the scanlines and sample data are actually in polar coordinates, but in FIG. 7, they have been collapsed for simple illustration where the scanlines are shown as being parallel to each other. Scan conversion must be performed on the raw ultrasound data frame of FIG. 7 to properly display the ultrasound image frame. The result of the scan conversion is the ultrasound image shown in FIG. 8, where the scanline and sample data in polar coordinates of FIG. 7 have been properly scan converted to X-Y coordinates to represent the curvature of the ultrasound scanner and the angle of trajectory of the ultrasound signals as they travel away from the scanhead (e.g., the signals get further apart the deeper ultrasound signal goes).

The systems and method described herein may be employed on the raw ultrasound data frame of FIG. 7 and the corresponding ultrasound image frame of FIG. 8. For example, an AI model may be trained to perform segmentation on the raw ultrasound data frame of FIG. 7 and other similar raw ultrasound data frames, so that the features (e.g., the dark circle on the upper middle portion of the image of FIG. 7) can be segmented and identified thereon. After scan conversion, the corresponding image features may be identified on the post-scan converted image.

Figure 9:
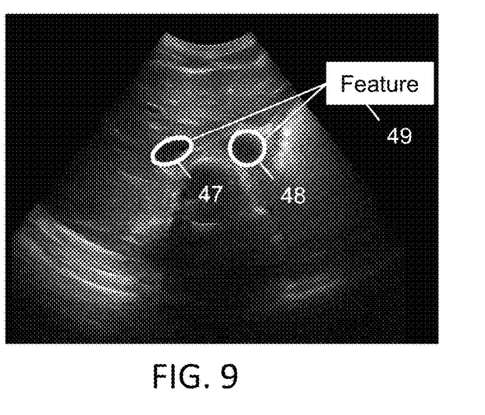
FIG. 9 is an ultrasound image, similar to that of FIG. 8, but which is segmented by an AI model trained to perform segmentation on the raw ultrasound data frame of FIG. 7 and has been scan converted, according to an embodiment of the present invention.

Referring to FIG. 9, shown there is an ultrasound image of abdominal tissue, acquired in a similar way to that of FIG. 8, but which is segmented to identify the anatomical feature predicted by the AI model that ran on FIG. 7. The feature identified in the raw ultrasound data frame of FIG. 7 may be transformed from the coordinate system of the raw ultrasound data frame to the coordinate system of the ultrasound image. This results in the segmentation 47, 48 on the ultrasound image of FIG. 9, which indicates predicted anatomical features that are identified by tag 49.

The training of the AI model may likewise be performed in a similar manner as discussed above for linear scanners. For example, labeling may be performed on post-scan converted images similar to what is shown in FIG. 8. And the identified features may be interpolated back to the coordinates of the raw ultrasound data frame so as to generate labeled raw ultrasound data frames that can be used to train the AI model.

Figure 10:
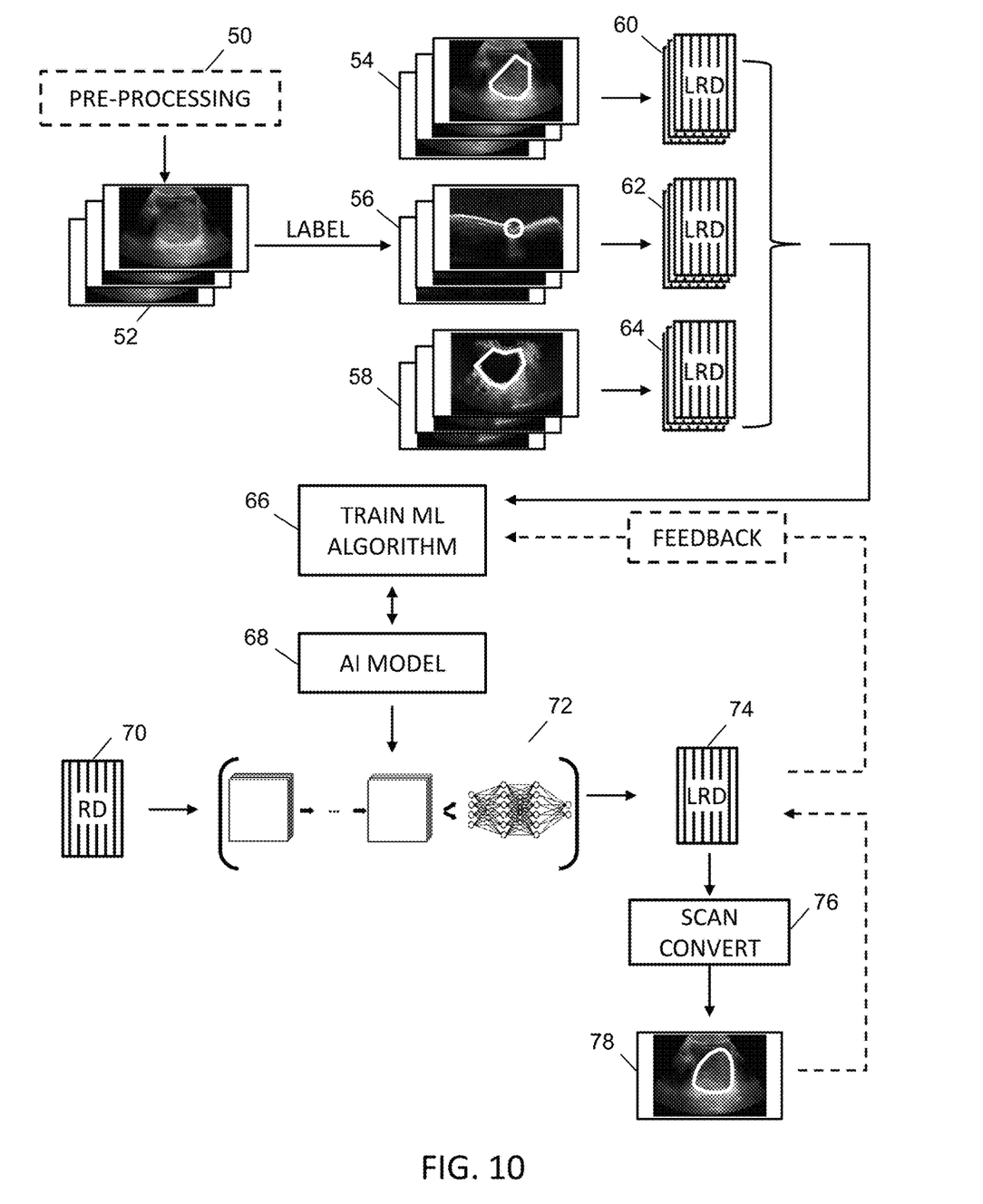
FIG. 10 is a schematic diagram of the training and deployment of an AI model, according to an embodiment of the present invention.

Referring to FIG. 10, a more fulsome flow diagram is shown for the training and deployment of the AI model 68 for the prediction of anatomical features in raw ultrasound data frames. The AI model 68 may generally be trained by labeled raw ultrasound data frames 60, 62, 64 (LRD, or labeled raw data) that each have a segmented portion of data corresponding to an anatomical feature. The labeled raw ultrasound data frames 60, 62, 64 are generated from back converting marked and labeled ultrasound images 54, 56, 58, and/or they are generated from the originating raw ultrasound data frames 52, into which the markings are interpolated.

To generate the labeled ultrasound images 54, 56, 58, a person such as an ultrasound image labeler is provided with ultrasound images 52. The labeler may then mark and label the ultrasound images 52 depending on the anatomical features that the labeler identifies in the ultrasound images 52. Additionally or alternatively, the labeler may accept or reject ultrasound images that are already segmented and labeled by another AI model, and/or the labeler may modify them before submitting them to be back converted to training samples. While the AI model 68 works with raw ultrasound data, the labeler generally does not need to look at the raw ultrasound data to do the labeling.

For example, some of the ultrasound images 52 may each have a common anatomical feature (e.g. a kidney), which may be marked by drawing a line around it and tagged by the name of the anatomical feature, leading to labeled ultrasound images 54. These in turn may be back converted to the labeled raw ultrasound data frames 60. Others of the ultrasound images 52 may each have another common anatomical feature (e.g. a fracture), which may be marked by drawing a line around it and tagged by the name of the anatomical feature, leading to labeled ultrasound images 56. These in turn may be back converted to the labeled raw ultrasound data frames 62. Yet more of the ultrasound images 52 may each have yet another common anatomical feature (e.g. a cyst), which is marked by drawing a line around it and tagged by the name of the anatomical feature, leading to labeled ultrasound images 58. These in turn may be back converted to the labeled raw ultrasound data frames 64.

In some embodiments, an optional pre-processing act 50 may be performed on the underlying ultrasound images 52 to facilitate improved performance and/or accuracy of the labeler. For example, it may be possible to pre-process the ultrasound images 52 through a high contrast filter to reduce the granularity of grayscale on the ultrasound images 52. Additionally or alternatively, it may be possible to change the scale of the ultrasound images 52 prior to displaying them to the labeler. It may also be possible to remove text such as a timestamp applied to the ultrasound images 52, and/or remove overlay data that may be present, such as parameters of the corresponding ultrasound scan. Various additional or alternative pre-processing acts may be performed in act 50. For example, these acts may include data normalization to ensure that the various ultrasound frames 52 used for displaying to the labeler have generally the same dimensions and parameters.

Referring still to FIG. 10, the various labeled raw ultrasound data frames 60, 62, 64 for training may, at act 66, be used to train a ML algorithm. For example, the various raw ultrasound data frames 60, 62, 64 may be inputted into a deep neural network that can learn how to predict the presence of anatomical features in raw ultrasound data frames. For example, the deep neural network may learn to detect, relative to surrounding tissue, the shape and brightness of raw image data that represents the presence of a plantar fascia.

The result of the training may be the AI model 68, which represents the mathematical weights and/or parameters learned by the deep neural network for predicting the presence of anatomical features in raw ultrasound data frames. The training act 66 may involve various additional acts (not shown) to generate a suitable AI model 68. For example, these may include various deep learning techniques such as regression, classification, feature extraction, and the like. Any generated AI models may be iteratively tested to ensure they are not overfitted and sufficiently generalized for predicting the presence of anatomical features in raw ultrasound data frames. In various embodiments, the machine learning may be supervised or unsupervised.

For example, in some embodiments, once the labeled raw ultrasound data frames for training are provided, a deep neural network may use them as inputs and the associated prediction of anatomical features as desired may be outputted to determine value sets of deep neural network parameters defining the deep neural networks.

In some embodiments, the deep neural network may be configured to receive one or more labeled raw ultrasound data frames as input and to have an output layer such as a softmax layer or a sigmoid layer containing outputs which represent whether scanlines/samples of the corresponding input data frame fall within the segmented portion of the data frame or not.

A file of the labeled raw ultrasound data frames for training may include an image identifier field for storing a unique identifier for identifying a labeled raw ultrasound data frame included in the file, a segmentation mask field for storing an identifier for specifying the portion of the predicted anatomical feature, and an image data field for storing information representing the image.

In some embodiments, using a cross-validation method on the training process would optimize deep neural network hyper-parameters to try to ensure that the deep neural network can sufficiently learn the distribution of all possible anatomical features without overfitting to the training data. In some embodiments, after finalizing the deep neural network architecture, the deep neural network may be trained on all of the data available in the training data files.

In various embodiments, batch training may be used and each batch may consist of multiple images, thirty-two for example, wherein each example raw ultrasound data frame may contain data in the form of scanlines by samples (e.g., scanlines along one axis and samples along a second axis), without any preprocessing applied to it.

In some embodiments, the deep neural network parameters may be optimized using the Adam optimizer with hyper-parameters as suggested by Kingma, D. P., Ba, J. L.:

Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the overfitting problem is dropout. Dropout layers limit the co-adaptation of the feature extracting blocks by removing some random units from the neurons in the previous layer of the deep neural network based on the probability parameter of the dropout layer. Moreover, this approach forces the neurons to follow overall behaviour. This implies that removing the units would result in a change in the deep neural network architecture in each training step. In other words, a dropout layer performs similar to adding random noise to hidden layers of the model. A dropout layer with the dropout probability of 0.5 may be used after the pooling layers.

Data augmentation is another approach to prevent overfitting and add more transitional invariance to the AI model. Therefore, in some embodiments, the training data frames may be augmented on-the-fly while training. In every minibatch, each training data frame may be truncated, and/or the scanline density reduced, for example.

Referring still to FIG. 10, after training has been completed, the sets of parameters stored in the storage memory may represent a trained deep neural network for predicting the presence of anatomical features in raw ultrasound data frames. In order to assess the performance of the AI model, the stored model parameter values can be retrieved any time to perform data frame assessment through applying a data frame to the deep neural networks represented thereby.

In some embodiments, the deep neural network may include various layers such as convolutional layers, max-pooling layers, and fully connected layers. In some embodiments, the final layers may include an output layer such as a softmax or sigmoid layer, with the output layer having outputs that eventually would demonstrate respective determinations that an input set of (scanline, sample) pairs fall within a particular area inside or outside of the segmentation. Accordingly, in some embodiments, the deep neural network may take at least one raw ultrasound data frame as an input and output a binary mask indicating which (scanline, sample) pair belong to a predicted anatomical feature (e.g., the AI model classifies which "area" each scanline, sample pair belongs to).

To increase the robustness of the AI model 68, in some embodiments, a broad set of training data may be used at act 66. For example, labeled raw ultrasound data frames for different ages and genders, and different stages of a medical condition can be included in the labeled raw ultrasound data frames 60, 62, 64 used for training. For example, in an example where the AI model 68 is to detect obstetrics/gynecology features, the training data may include labeled raw ultrasound data frames for early obstetrics (OB) (up to 8 weeks), mid OB (between 8 and 26 weeks) and late OB (after 26 weeks). Markings may be identified on the ultrasound images from which the labeled raw ultrasound data frames are derived. These markings can then be back converted to the coordinates of the raw ultrasound data frame during training, so that the AI model 68 can learn to generate the segmentation of the raw ultrasound data frames regardless of the patient's age, gender, extent of medical condition and stage of pregnancy.

Additionally or alternatively, in some embodiments, the training act 66 in FIG. 10 may be repeated with different datasets for the different anatomical features to generate corresponding different AI models 68 that each generate segmentations for a specific anatomical feature in the raw ultrasound data frames, or a specific medical condition, or a specific symptom, for example. In this scenario, the appropriate AI model 68 can be selected to be applied based on a known medical condition or symptom.

In these example embodiments where the training datasets include anatomical features at different stages, the resulting AI model(s) 68 may be more robust. This is because anatomical features at some stages may be easier to distinguish from surrounding tissue than anatomical features at other stages. By having the dataset include these scenarios, the AI model 68 (if only a single AI model 68 is generated) may learn to recognize these situations so as to produce accurate segmentations at multiple stages of an anatomical feature.

Referring still to FIG. 10, once a satisfactory AI model 68 is generated, the AI model 68 may be deployed for execution on a deep neural network 72 to predict the presence of anatomical features in raw ultrasound data frames 70 (RD, or raw data). Notably, the deep neural network 72 is shown in FIG. 10 for illustration as a convolution neural network—with various nodes in the input layer, hidden layers, and output layers. However, in various embodiments, different arrangements of the deep neural network 72 may be possible.

In various embodiments, the raw ultrasound data frames 70 may be live data frames acquired by an ultrasound imaging system (e.g., the system discussed with respect to FIG. 12 below). For example, the AI model 68 may be deployed for execution on the scanner 131 and/or the display device 150 discussed in more detail below. Additionally or alternatively, the AI model 68 may be executed on stored raw ultrasound data frames 70 that were previously acquired. When executed, the AI model 68 may allow the deep neural network 72 to predict anatomical features in raw ultrasound data frames 70, resulting in a series of labeled raw ultrasound date frames 74 with predicted anatomical features defined therein. The labeled raw ultrasound date frames 74 with predicted anatomical features may then be scan converted 76 and used for the generation of viewable, segmented ultrasound images 78.

In some embodiments, ultrasound images 78 with segmented anatomical features may optionally each be labeled as either acceptable or unacceptable, and these labeled ultrasound images 78 may themselves be used for training and/or reinforcing the AI model 68. For example, the segmented scan converted image 78 (e.g., another example of which was shown as segmented ultrasound image 42 in FIG. 6) may be labeled as acceptable or unacceptable, back converted to the format of the labeled raw ultrasound data frame 74, which in turn may be used for training and/or reinforcing the AI model 68. This is shown in FIG. 10 with dotted lines from the segmented ultrasound image 78 to the raw ultrasound data frame 74 and then feeding back to the training act 66.

The AI model 68, once trained, may be exported to work on any other format of raw ultrasound data frame for use in other scanners that operate on a different standard format of scan lines and samples.

Figure 11:
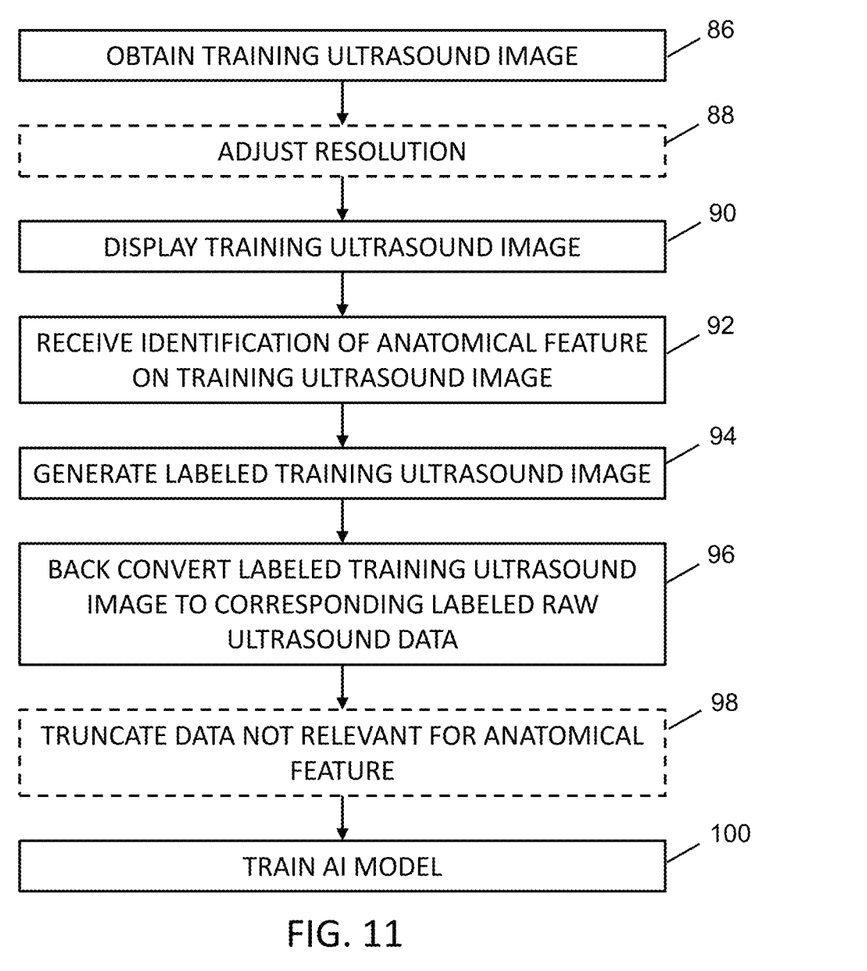
FIG. 11 is a flowchart of the steps for training the AI model, according to an embodiment of the present invention.

Referring to FIG. 11, a flowchart is seen for an exemplary method of training the AI model 68 of FIG. 10. In step 86, a training ultrasound image may be obtained. For example, a training ultrasound image may be acquired by the scanner 131 (as shown in FIG. 12) transmitting and receiving ultrasound energy. The training ultrasound image may generally be a post-scan converted ultrasound image. While the method of FIG. 11 is described in relation to a single training ultrasound image, the method may also apply to the use of multiple training ultrasound images.

Optionally, in step 88 (as shown in dotted outline), the resolution of the training ultrasound image may be adjusted. For example, the resolution may be increased or decreased. The purpose of this may be to provide the labeler with training ultrasound images that have a more standardized appearance. This may help to maintain a higher consistency with which the labeler identifies anatomical features in the training ultrasound images. Besides the resolution, other parameters of the training ultrasound image may also be adjusted such as input scaling, screen size, pixel size, aspect ratio, and the removal of dead space.

In step 90, the training ultrasound image may be displayed on a display device, such as the display device 150 discussed in more detail below in relation to FIG. 12. The labeler can then identify a particular anatomical feature in the training ultrasound image by, for example, tagging it with a name from a pull-down menu (e.g., as described above in relation to FIGS. 2 and 3). The labeler then can mark the training ultrasound image around the particular anatomical feature that the labeler has identified in the training ultrasound image. Again, the labeler may use techniques such as those described above in relation to FIGS. 2 and 3. In step 92, the system that is used for the training may receive the identification of the particular anatomical feature. In step 94, the system may generate, from the labeler's marking inputs, a labeled training ultrasound image, and display it on the display device. In various embodiments, steps 92 and 94 may readily be interchanged with each other.

Once the training ultrasound image has been marked and labeled, the system may then, in step 96, back convert the labeled training ultrasound image, as represented in x-y coordinates suitable for human viewing, to the coordinate system of the raw ultrasound data frame from which the training ultrasound image was originally scan converted. The back conversion includes, for example, transforming the coordinates of the marking to the coordinate system of the raw ultrasound data frame and associating them with the raw ultrasound data frame that was scan converted to result in the training ultrasound data frame. The back conversion may include, in other embodiments, transforming both the ultrasound image and the coordinates of the marking to the coordinate system of the raw ultrasound data frame. Furthermore, by back converting to a standard size of raw ultrasound data frame, the labeled raw ultrasound data frames may provide a more standardized "appearance" for training the AI model about the shape, size, and other parameters of the anatomical feature. This, in turn may allow for the training to be more accurate and converge more quickly than if a range of different sizes of raw ultrasound data frames were used.

Optionally, in step 98 (as shown in dotted outline), regions of the labeled raw ultrasound data frame that are both outside the area of the identified anatomical feature and outside areas relevant for the AI model to recognize the particular anatomical feature may be removed. For example, the labeled raw ultrasound data frame may be truncated at one or more sides. Additionally or alternatively, the data at deeper depths on labeled raw ultrasound data frame may be truncated if the anatomical feature is at a relatively shallower portion of the labeled raw ultrasound data frame. Truncation of some of the raw ultrasound data may allow the training of the AI model to proceed more quickly. In step 100, the labeled raw ultrasound data frame is then used for training the AI model.

Figure 12:
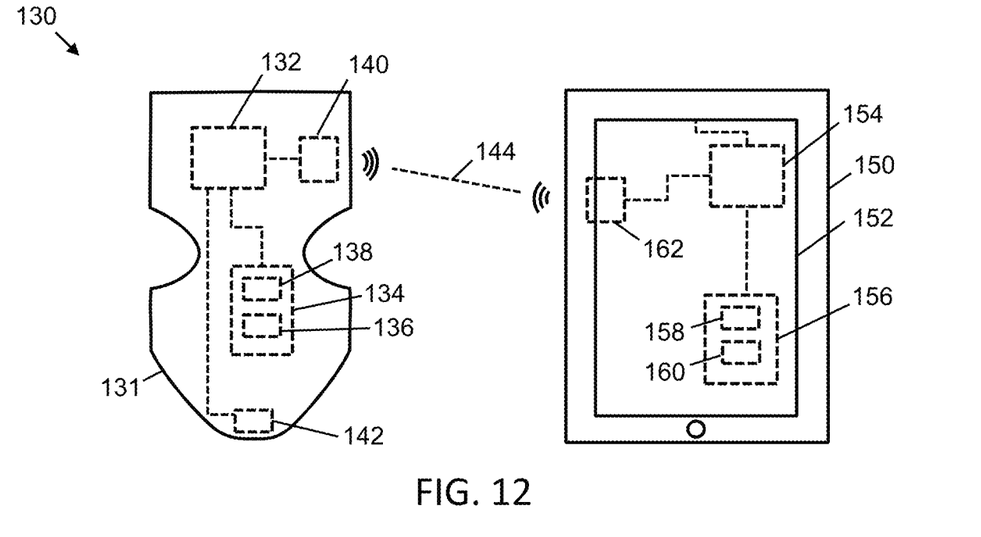
FIG. 12 is a schematic diagram of an ultrasound imaging system for the training and deployment of an AI model that segments raw ultrasound data frames, according to an embodiment of the present invention.

Referring to FIG. 12, an exemplary system 130 is shown for displaying an ultrasound image segmented with a representation of a predicted anatomical feature. The system 130 includes an ultrasound scanner 131 with a processor 132, which is connected to a non-transitory computer readable memory 134 storing computer readable instructions 136, which, when executed by the processor 132, may cause the scanner 131 to provide one or more of the functions of the system 130. Such functions may be, for example, the acquisition of ultrasound data, the processing of ultrasound data, the prediction of anatomical features in raw ultrasound data frames, the scan conversion of ultrasound data, the transmission of ultrasound data or ultrasound frames to a display device 150, the detection of operator inputs to the ultrasound scanner 131, and/or the switching of the settings of the ultrasound scanner 131. The prediction of anatomical features in the raw ultrasound data frames may be performed in real time by the scanner 131.

Also stored in the computer readable memory 134 may be computer readable data 138, which may be used by the processor 132 in conjunction with the computer readable instructions 136 to provide the functions of the system 130. Computer readable data 138 may include, for example, configuration settings for the scanner 131, such as presets that instruct the processor 132 how to collect and process the ultrasound data for a given body part, how to acquire a series of ultrasound frames, and/or the AI model 68.

The scanner 131 may further include an ultrasonic transducer 142 (e.g., made up of piezoelectric elements, capacitive micromachined ultrasonic transducer (CMUT) elements, piezoelectric micromachined ultrasonic transducer (PMUT) elements, or other technology that performs the same function) for transmitting and receiving ultrasound signals that generate the raw ultrasound data frame and corresponding ultrasound image frame.

The scanner 131 may include a communications module 140 connected to the processor 132. In the illustrated example, the communications module 140 may wirelessly transmit signals to and receive signals from the display device 150 along wireless communication link 144. The protocol used for communications between the scanner 131 and the display device 150 may be WiFi™ or Bluetooth™, for example, or any other suitable two-way radio communications protocol. In some embodiments, the scanner 131 may operate as a WiFi™ hotspot, for example. Communication link 144 may use any suitable wireless communications network connection. However, in some embodiments, the communication link between the scanner 131 and the display device 150 may be wired. For example, the scanner 131 may be attached to a cord that may be pluggable into a physical port of the display device 150.

In various embodiments, the display device 150 may be, for example, a laptop computer, a tablet computer, a desktop computer, a smart phone, a smart watch, spectacles with a built-in display, a television, a bespoke display or any other display device that is capable of being communicably connected to the scanner 131. The display device 150 may host a screen 152 and may include a processor 154, which may be connected to a non-transitory computer readable memory 156 storing computer readable instructions 158, which, when executed by the processor 154, cause the display device 150 to provide one or more of the functions of the system 130. Such functions may be, for example, the receiving of ultrasound data that may or may not be pre-processed; scan conversion of received ultrasound data into an ultrasound image; processing of ultrasound data in image data frames; the display of a user interface; the control of the scanner 131; the display of an ultrasound image on the screen 152; the prediction of anatomical features in raw ultrasound data frames; the generation of labeled ultrasound images from labeled raw ultrasound data frames; the generation of labeled ultrasound images from user inputs; and/or the storage, application, reinforcing and/or training of an AI model 68 that predicts the presence of anatomical features in raw ultrasound data frames.

Also stored in the computer readable memory 156 may be computer readable data 160, which may be used by the processor 154 in conjunction with the computer readable instructions 158 to provide the functions of the system 130. Computer readable data 160 may include, for example, settings for the scanner 131, such as presets for acquiring ultrasound data; settings for a user interface displayed on the screen 152; and/or data for one or more AI models 68 for predicting the presence of anatomical features in raw ultrasound data frames. Settings may also include any other data that is specific to the way that the scanner 131 operates and/or that the display device 150 operates.

It can therefore be understood that the computer readable instructions and data used for controlling the system 130 may be located either in the computer readable memory 134 of the scanner 131, the computer readable memory 156 of the display device 150, and/or both the computer readable memories 134, 156.

The display device 150 may also include a communications module 162 connected to the processor 154 for facilitating communication with the scanner 131. In the illustrated example, the communications module 162 wirelessly transmits signals to and receives signals from the scanner 131 on wireless communication link 144. However, as noted, in some embodiments, the connection between scanner 131 and display device 150 may be wired.

Figure 13:
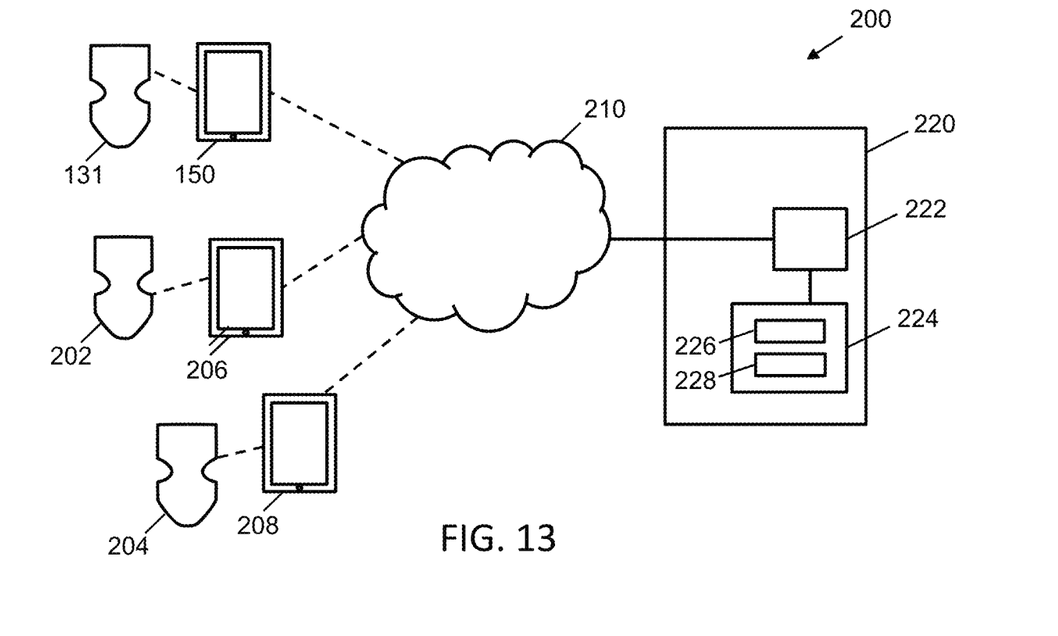
FIG. 13 is a schematic diagram of a system with multiple training interfaces, according to an embodiment of the present invention.

Referring to FIG. 13, a system 200 is shown in which there are multiple similar or different display devices 150, 206, 208 (paired respectively to scanners 131, 202, 204) connected directly (or indirectly) to a communications network 210, such as the Internet. Each display device 150, 206, 208 may be used for training the AI model 68. The scanners 131, 202, 204 and display devices 150, 206, 208 may be connected onwards via the communications network 210 to a server 220.

The server 220 may include a processor 222, which may be connected to a non-transitory computer readable memory 224 storing computer readable instructions 226, which, when executed by the processor 222, cause the server 220 to provide one or more of the functions of the system 200. Such functions may be, for example, the receiving of raw ultrasound frames, the processing of ultrasound data in raw ultrasound data frames, the processing of markings and tags associated with anatomical features in ultrasound images, the control of scanners 131, 202, 204, the prediction of anatomical features in raw ultrasound data frames using an AI model, and/or machine learning activities related to one or more AI models 68 (as discussed above in relation to FIG. 10). Such machine learning activities may include the training and/or reinforcing of one or more AI models 68 for predicting anatomical features in raw ultrasound data frames.

Also stored in the computer readable memory 224 may be computer readable data 228, which may be used by the processor 222 in conjunction with the computer readable instructions 226 to provide the functions of the system 200. Computer readable data 228 may include, for example, settings for the scanners 131, 202, 204, such as preset parameters for acquiring ultrasound data, settings for user interfaces displayed on the display devices 150, 206, 208, and data for one or more AI models 68. For example, the AI model 68 may be used to predict anatomical features in raw ultrasound data frames, as discussed above. Settings may also include any other data that is specific to the way that the scanners 131, 202, 204 operate or that the display devices 150, 206, 208 operate.

It can therefore be understood that the computer readable instructions and data used for controlling the system 200 may be located either in the computer readable memory of the scanner 131 (or multiple scanners that also include scanners 202, 204) the computer readable memory of the display devices 150, 206, 208, the computer readable memory 224 of the server 220, or any combination of the foregoing locations.

As noted above, even though the display devices 150, 206, 208 may be different, each labeled ultrasound image created thereon may be used by the AI model 68 for training. Likewise, the raw ultrasound data frames acquired by multiple scanners 131, 202, 204 may all be processed against the AI model 68 for prediction of the anatomical features and/or for reinforcement of the AI model 68.

In some embodiments, the AI models 68 present in the scanner 131 or display devices 150, 206, 208 may be updated from time to time from an AI model 68 present in the server 220, where the AI model 68 present in the server 220 is continually trained using labeled raw ultrasound data frames acquired by multiple scanners 131, 202, 204.

While the invention has been describe in relation to anatomical features it may also have application in the field of identifying foreign objects in living tissue. Such foreign objects may include, for example, surgical tools accidentally left in the body after surgery and metallic objects such as coins that a child may swallow.

The invention may also find application in other areas of medical scanning, such as MRI (magnetic resonance imaging), CT (computed tomography) and certain x-rays, in which the raw scan data is in a coordinate system that is different to the coordinate system in which the image is presented to a human reviewer.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The embodiments may also be provided in the form of a program product. The program product may include any non-transitory medium which carries a set of computer-readable instructions which, when executed by a data processor, cause the data processor to execute a method of the invention. Program products according to the invention may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and sub-combinations as may reasonably be inferred. The scope of the claims should not be limited by the embodiments set forth in the examples but should be given the broadest interpretation consistent with the description as a whole.

C. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the examples described and illustrated. The subject matter described herein may assume various alternative orientations. Accordingly, these directional terms are not strictly defined and should not be interpreted narrowly.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

D. Claim Support

Disclosed herein is a method for displaying a predicted anatomical feature in an ultrasound image comprising: acquiring a raw ultrasound data frame using an ultrasound scanner; processing the raw ultrasound data frame against an AI model to predict a presence of an anatomical feature imaged in the raw ultrasound data frame; determining, by the AI model, raw data coordinates of the predicted anatomical feature imaged in the raw ultrasound data frame; scan converting the raw ultrasound data frame to an ultrasound image; transforming the raw data coordinates of the predicted anatomical feature to x-y coordinates in the ultrasound image; and displaying the ultrasound image segmented with a representation of the x-y coordinates of the predicted anatomical feature.

In some embodiments, the processing of the raw ultrasound data frame against the AI model is performed by the ultrasound scanner.

In some embodiments, the scan converting, the transforming and the displaying are performed by a display device.

In some embodiments, the method comprises, before the acquiring step: receiving, by a processor, a training ultrasound image and an identification of an example of the anatomical feature in the training ultrasound image, wherein the training ultrasound image is converted from a raw ultrasound training data frame; transforming, by the processor, x-y coordinates of the example of the anatomical feature identified in the training ultrasound image to raw training data coordinates in a coordinate system of the raw ultrasound training data frame; and training, by the processor, the AI model or a duplicate thereof with the raw training data coordinates and the raw ultrasound training data frame.

In some embodiments, the training ultrasound image is one of a set of training ultrasound images; and the receiving, transforming and training steps are performed for each of the training ultrasound images in the set of training ultrasound images.

In some embodiments, the method comprises, prior to the receiving step: displaying the training ultrasound image; and receiving input identifying the anatomical feature on the training ultrasound image.

In some embodiments, the raw data coordinates and the raw training data coordinates are polar coordinates.

In some embodiments, the x-y coordinates of the example of the anatomical feature form a mask, and the x-y coordinates of the predicted anatomical feature form another mask.

In some embodiments, the training ultrasound image is a center image of a compound image.

In some embodiments, the input identifying the example of the anatomical feature is a tracing around all or part of the anatomical feature.

In some embodiments, the raw ultrasound data frame and the raw ultrasound training data frame have identical pixel array dimensions.

In some embodiments, the method comprises, reducing a resolution of the raw ultrasound training data frame and a resolution of the raw training data coordinates of the example of the anatomical feature identified in the training ultrasound image before training the AI model; and reducing a resolution of the raw ultrasound data frame before processing with the AI model.

In some embodiments, the AI model comprises a segmentation function, a classification function or both a segmentation function and a classification function.

In some embodiments, the training step comprises supervised learning.

In some embodiments, the method comprises, predicting a presence of a further anatomical feature in the ultrasound image.

In some embodiments, the anatomical feature is an organ, a portion of an organ, a boundary of an organ, a bodily fluid, a tumor, a cyst, a fracture, or a break.

Also disclosed herein is a system for displaying a predicted anatomical feature in an ultrasound image comprising: an ultrasound scanner configured to: acquire a raw ultrasound data frame; process the raw ultrasound data frame against an AI model to predict a presence of an anatomical feature imaged in the raw ultrasound data frame; and determine raw data coordinates of the predicted anatomical feature imaged in the raw ultrasound data frame; and a display device configured to: scan convert the raw ultrasound data frame to an ultrasound image; transform the raw data coordinates of the predicted anatomical feature to x-y coordinates in the ultrasound image; and display the ultrasound image segmented with a representation of the x-y coordinates of the predicted anatomical feature.

In some embodiments, the system comprises, a processor configured, before acquiring the raw ultrasound data frame, to: receive a training ultrasound image and an identification of an example of the anatomical feature in the training ultrasound image, wherein the training ultrasound image is converted from a raw ultrasound training data frame; transform x-y coordinates of the example of the anatomical feature identified in the training ultrasound image to raw training data coordinates in a coordinate system of the raw ultrasound training data frame; and train the AI model or a duplicate thereof with the raw training data coordinates and the raw ultrasound training data frame.

In some embodiments, the processor is configured, prior to receiving the training ultrasound image, to: display the training ultrasound image; and receive input identifying the anatomical feature on the training ultrasound image.

In some embodiments, the processor is configured to: reduce a resolution of the raw ultrasound training data frame and a resolution of the raw training data coordinates of the example of the anatomical feature identified in the training ultrasound image before training the AI model; and reduce a resolution of the raw ultrasound data frame before processing with the AI model.

The invention claimed is:

1. A method for displaying a predicted anatomical feature in an ultrasound image comprising:
   acquiring a raw ultrasound data frame, which is organized using raw data coordinates, using a non-invasive ultrasound scanner which comprises a plurality of transducer elements, wherein the acquiring comprises activation of two or more transducer elements of the plurality of transducer elements,
   deploying an artificial intelligence model to execute on a computing device, communicably connected to the non-invasive ultrasound scanner, wherein the AI model is trained to predict a presence of an anatomical feature imaged in the raw ultrasound data frame;
   processing, by the computing device, the raw ultrasound data frame against the AI model to: i) predict a presence of an anatomical feature imaged in the raw ultrasound data frame; and ii) determine raw data coordinates of the predicted anatomical feature imaged in the raw ultrasound data frame;
   scan converting the raw ultrasound data frame to an ultrasound image that is suitable for rendering on a display device;
   transforming the raw data coordinates of the predicted anatomical feature to x-y coordinates in the ultrasound image; and
   displaying the ultrasound image segmented with a representation of the x-y coordinates of the predicted anatomical feature.

2. The method of claim 1, wherein the processing of the raw ultrasound data frame against the AI model is performed by the non-invasive ultrasound scanner.

3. The method of claim 1, wherein the scan converting, the transforming and the displaying are performed by the display device.

4. The method of claim 1, comprising, before the acquiring step:

receiving, by a processor, a training ultrasound image and an identification of an example of the anatomical feature in the training ultrasound image, wherein the training ultrasound image is converted from a raw ultrasound training data frame;

transforming, by the processor, x-y coordinates of the example of the anatomical feature identified in the training ultrasound image to raw training data coordinates in a coordinate system of the raw ultrasound training data frame; and training, by the processor, the AI model or a duplicate thereof with the raw training data coordinates and the raw ultrasound training data frame.

5. The method of claim 4, wherein:
the training ultrasound image is one of a set of training ultrasound images; and
the receiving, transforming and training steps of claim 4 are performed for each of the training ultrasound images in the set of training ultrasound images.

6. The method of claim 4, comprising, prior to the receiving step:
displaying the training ultrasound image; and
receiving input identifying the anatomical feature on the training ultrasound image.

7. The method of claim 4, wherein the raw data coordinates and the raw training data coordinates are polar coordinates.

8. The method of claim 4, wherein the x-y coordinates of the example of the anatomical feature form a mask, and the x-y coordinates of the predicted anatomical feature form another mask.

9. The method of claim 4, wherein the input identifying the example of the anatomical feature is a tracing around all or part of the anatomical feature.

10. The method of claim 4, wherein the raw ultrasound data frame and the raw ultrasound training data frame have identical pixel array dimensions.

11. The method of claim 4, comprising:
reducing a resolution of the raw ultrasound training data frame and a resolution of the raw training data coordinates of the example of the anatomical feature identified in the training ultrasound image before training the AI model; and
reducing a resolution of the raw ultrasound data frame before processing with the AI model.

12. The method of claim 4, wherein the AI model comprises a segmentation function, a classification function or both a segmentation function and a classification function.

13. The method of claim 4, wherein the training step comprises supervised learning.

14. The method of claim 1, wherein the anatomical feature is an organ, a portion of an organ, a boundary of an organ, a bodily fluid, a tumor, a cyst, a fracture, or a break.

15. A system for displaying a predicted anatomical feature in an ultrasound image comprising:
a non-invasive ultrasound scanner comprising a plurality of transducer elements and configured to:
acquire a raw ultrasound data frame, which is organized using raw data co-ordinates, wherein the acquiring comprises activation of two or more transducer elements of the plurality of transducer elements;
process the raw ultrasound data frame against an AI model to i) predict a presence of an anatomical feature imaged in the raw ultrasound data frame; and ii) determine raw data coordinates of the predicted anatomical feature imaged in the raw ultrasound data frame, wherein the AI model is trained to predict a presence of an anatomical feature imaged in the raw ultrasound data frame; and
a display device, communicably connected to the non-invasive ultrasound scanner, configured to:
scan convert the raw ultrasound data frame to an ultrasound image that is suitable for rendering on the display device;
transform the raw data coordinates of the predicted anatomical feature to x-y coordinates in the ultrasound image; and
display the ultrasound image segmented with a representation of the x-y coordinates of the predicted anatomical feature.

16. The system of claim 15 comprising a processor configured, before acquiring the raw ultrasound data frame, to:
receive a training ultrasound image and an identification of an example of the anatomical feature in the training ultrasound image, wherein the training ultrasound image is converted from a raw ultrasound training data frame;
transform x-y coordinates of the example of the anatomical feature identified in the training ultrasound image to corresponding raw training data coordinates in a coordinate system of the raw ultrasound training data frame; and
train the AI model or a duplicate thereof with the raw training data coordinates and the raw ultrasound training data frame.

17. The system of claim 16, wherein the processor is configured, prior to receiving the training ultrasound image, to:
display the training ultrasound image; and
receive input identifying the anatomical feature on the training ultrasound image.

18. The system of claim 16, wherein the raw ultrasound data frame and the raw ultrasound training data frame have identical pixel array dimensions.

19. The system of claim 16, wherein the processor is configured to:
reduce a resolution of the raw ultrasound training data frame and a resolution of the raw training data coordinates of the example of the anatomical feature identified in the training ultrasound image before training the AI model; and
reduce a resolution of the raw ultrasound data frame before processing with the AI model.

20. The system of claim 16, wherein the AI model comprises a segmentation function, a classification function or both a segmentation function and a classification function.

* * * * *